United States Patent [19]

Scott

[11] 4,301,603
[45] Nov. 24, 1981

[54] WATER IMPERVIOUS BOOT FOR PROTECTING A SURGICAL CAST

[76] Inventor: Dalbert B. Scott, 3201 Vista Cielo La., Spring Valley, Calif. 92077

[21] Appl. No.: 173,766

[22] Filed: Jul. 29, 1980

Related U.S. Application Data

[63] Continuation of Ser. No. 26,318, Apr. 2, 1979, abandoned.

[51] Int. Cl.³ .......................... A43B 7/12; A61F 13/00
[52] U.S. Cl. ........................................ 36/110; 36/7.3; 36/8.1; 36/57; 128/82
[58] Field of Search ...................... 36/110.1, 8.1, 7.3, 36/57, 7.1; 128/82, 83.5

[56] References Cited

U.S. PATENT DOCUMENTS

| | | | |
|---|---|---|---|
| 1,715,120 | 5/1929 | Costellow | 36/7.3 |
| 2,423,354 | 7/1947 | Van Hoesen | 36/1 |
| 2,582,648 | 1/1952 | Mowbray | 36/8.1 |
| 3,228,819 | 1/1966 | Bingham Jr. | 36/7.3 X |
| 3,500,560 | 3/1970 | Drazen | 36/57 |
| 3,735,758 | 5/1973 | Novotney | 128/82 |
| 3,741,203 | 6/1973 | Liman | 128/82 |
| 3,802,424 | 4/1974 | Newell | 128/83.5 X |
| 4,098,268 | 7/1978 | Scott | 128/82 |
| 4,178,924 | 12/1979 | Baxter | 128/82 |

FOREIGN PATENT DOCUMENTS

| | | | |
|---|---|---|---|
| 1564135 | 3/1969 | France | 36/7.3 |
| 23810 | of 1905 | United Kingdom | 36/57 |

Primary Examiner—James Kee Chi
Attorney, Agent, or Firm—Brown & Martin

[57] ABSTRACT

A light weight flexible boot to be worn over a foot in a surgical cast and protect the cast from moisture. The boot has a walking sole of tough rubber type material with a cushion sole and an upper body composed entirely of flexible and elastic foam material, with an inner fabric layer and an outer covering of water impervious fabric. The boot can be stretched over various sizes and shapes of casts and all joints in the boot are completely sealed and waterproof.

9 Claims, 4 Drawing Figures

WATER IMPERVIOUS BOOT FOR PROTECTING A SURGICAL CAST

This is a continuation of application Ser. No. 26,318 filed Apr. 2, 1979, now abandoned.

BACKGROUND OF THE INVENTION

Surgical casts on the foot and lower leg are often applied so that the wearer can walk on the affected leg, with appropriate care. Some casts are made with a small stud or foot built in to hold the cast off the ground. This makes walking difficult since one leg is then effectively larger than the other. It is also common practice to wear a thick sock or a cut away shoe over the cast for protection. However, none of these techniques will keep a cast dry, particularly if it becomes necessary to walk through a puddle, or in snow.

The inventor has a U.S. Pat. No. 4,098,268 entitled "Water Impervious Cover For An Arm Or Leg Cast", which discloses an elongated sheath for completely covering a cast. The open end is sealed by pulling a strap tight and the interior may be inflated. This particular protector permits total immersion of the limb in water, as in a therapeutic bath. However, such total protection is not always necessary and for walking in rain or snow, a simple slip on boot would be sufficient.

SUMMARY OF THE INVENTION

The protective boot described herein, is a simple slip on boot with a walking sole of tough rubber type material and an upper body of flexible and elastic foam material. The exterior of the body has a bonded covering of water impervious fabric, such as closely woven nylon, which also strengthens the body. The inside of the body also has a bonded layer of soft fabric for comfort and wear resistance and a fabric covered foam cushion inner sole is secured to the walking sole. All seams and joints in the construction are completely sealed by a water impervious adhesive, the peripheral joint of the body to the sole and the seams in the body also being stitched for strength. The boot has sufficient elasticity to be stretched over casts of different sizes and shapes with minimum effort.

The primary object of this invention is to provide a new and improved water impervious boot for protecting a surgical cast.

Another object of this invention is to provide a cast protecting boot having a walking sole and a light weight upper body of flexible foam material.

A further object of this invention is to provide a cast protecting boot which is covered and strengthened by water impervious fabric.

Other objects and advantages will be apparent in the following detailed description, taken in conjunction with the accompanying drawings, in which.

DESCRIPTION OF THE PREFERRED EMBODIMENT

Figure 1:
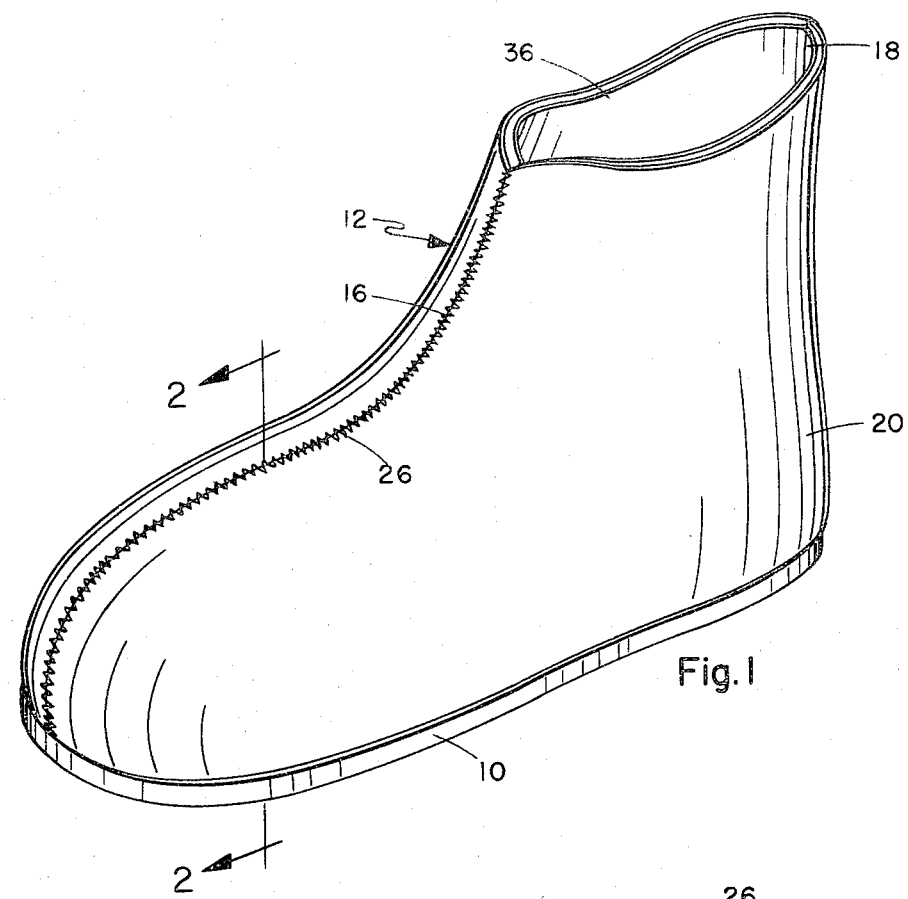
FIG. 1 is a perspective view of the protective boot.
Figure 2:
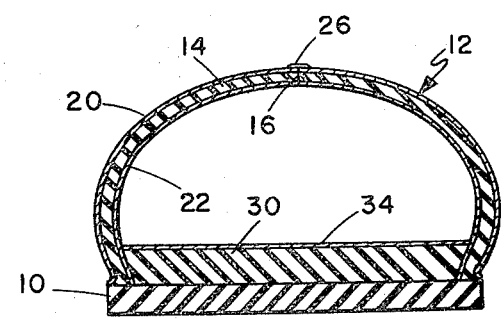
FIG. 2 is a sectional view taken on line 2—2 of FIG. 1.

The boot has a sole 10 of tough rubber type material to withstand the wear of walking, and a light weight flexible upper body 12. The boot may be made in various sizes and the body is shaped to enclose a foot in a cast. As illustrated, the boot would extend slightly above the ankle, but could be made higher. However, the boot must be easy to slip on over a cast without having an unduly large leg portion and upper end opening. The underside of the sole may be provided with any suitable non-slip surface or tread configuration.

Body 12 is made with a flexible foam shell 14 of Neoprene or similar resilient material, which is soft and tear resistant and will hold a particular shape without permanent deformation. The body can be made in several pieces and is illustrated as being made in two sides joined at front and rear seams 16 and 18, respectively.

The exterior of the body 12 is covered by a water impervious fabric layer 20 integral with or bonded to the foam shell. Fabric layer 20 is preferably of closely woven nylon, or the like, the material being well known in the construction of wet suits for divers. For comfort and strength the interior of the body is covered by an inner fabric layer 22 of soft material, bonded to the foam shell. One such material, comprising the foam with fabric on both sides, is readily available and is sold under the trade name of Rubitex G-231.

Figure 4:
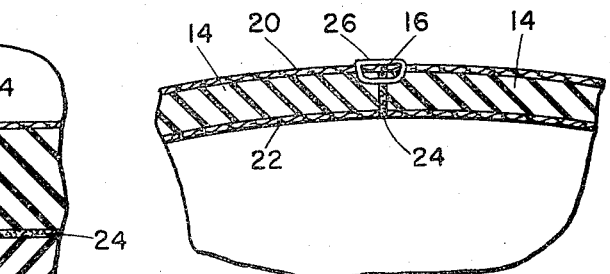
FIG. 4 is an enlarged sectional view of a typical body seam.

The front and rear seams are made as typified by seam 16 in FIG. 4. The edges of the foam shell 12 are butt jointed by a waterproof adhesive 24 and the entire length of the seam is overstitched by stitching 26 through the outer fabric layer 20.

Figure 3:
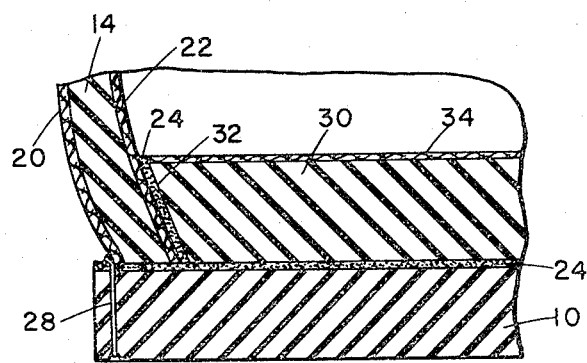
FIG. 3 is an enlarged sectional view of the upper body to sole joint.

In the junction of the body 12 to sole 10, the entire periphery of the shell 14 is butt jointed to the top surface of the sole by waterproof adhesive 24. For strength the entire periphery of the body is also secured to the sole by stitching 28 through the outer fabric layer 20 and the sole 10, as in FIG. 3.

A resilient inner sole 30, of foam Neoprene or the like, is bonded to the top surface of sole 10 by adhesive 24, and is also bonded by the adhesive to the inner surface of body 12 around the entire inner periphery of the body. The outer edge 32 of the inner sole 30 is cut at an angle, as in FIG. 3, to fit closely against the contoured inner surface of the body and provide maximum bonding area. The top surface of inner sole 30 is covered by a fabric layer 34, of material similar to inner layer 22.

It should be noted that the adhesive 24 is shown as having a definite thickness for purposes of illustration. In manufacture, the bonding would be performed by a solvent to provide an adhesively welded joint with no actual separation of the parts.

While dimensions are not critical, details of the various parts will serve to indicate the versatility and function of the boot. The body material, for example, has a foam core about ⅛ to 5/32 of an inch in thickness, while the foam inner sole is about ¼ to ⅜ of an inch thick to protect the cast under the weight of the wearer.

The sole is from 3/16 to ¼ of an inch thick and while being tough and considerably harder than the foam, is still flexible enough to facilitate pulling the boot on over a cast. The elasticity of the body material allows stretching to pass over a cast, while keeping the leg opening 36 small enough to fit closely around the leg and prevent water from dripping inside the boot. It has been found that when putting the boot on, the fit is usually tight enough over a cast that air is trapped in the boot and forms a cushion around the foot. This air pocket reduces perspiration compared to that experienced in an overall tight fitting impermeable covering.

The flexible and elastic body makes it possible to retain the boot in place over a variety of casts, without the need for straps or fasteners.

By adhesively sealing all portions of the structure together, the boot becomes a unitary water impervious envelope, which allows the wearer to wade through puddles or walk in snow without getting the cast wet. The cushioned walking sole provides good protection for the cast and extends the useful life of the boot. The inner fabric layer adds to the strength of the boot and protects the foam shell from wear by any rough spots on the cast. Usually the wearer would wear a light sock over the foot for added comfort, but this is not essential.

When constructed as described, the boot is machine washable, and due to the strength and wear resistance incorporated in the structure, can be used a number of times.

Having described my invention, I now claim:

1. A water impervious boot for protecting a surgical cast comprising:
    a walking sole of tough, flexible rubber-like material;
    an upper body of elastic material shaped to enclose a casted foot and being peripherally sealed to said sole;
    said body having a shell of resilient foam material with an outer layer of fabric integral therewith;
    said body being in sections joined at at least one seam, each seam being adhesively bonded and stitched together by stitching through said outer fabric layer on both sides of said seam and into said resilient foam material without penetrating the inner surface of said foam material.

2. A boot according to claim 1, wherein said body is peripherally stitched to said walking sole by stitching through the walking sole and through said outer fabric layer.

3. A boot according to claim 1 wherein:
    said seams are permanently joined and form said body into a continuous, substantially uninterrupted surface.

4. A boot according to claim 2, and including a resilient inner sole bonded to said walking sole.

5. A boot according to claim 4 wherein:
    said walking sole is substantially harder than said inner sole.

6. A boot according to claim 4, wherein said inner sole is adhesively sealed peripherally to said body.

7. A boot according to claim 6 wherein said body has an inner fabric layer bonded to said shell, said inner fabric layer comprising the innermost and cast-contacting layer of said shell.

8. A boot according to claim 7, wherein said inner sole has an upper fabric layer thereon.

9. A boot according to claim 1 wherein:
    said upper body consisting of a plurality of layers joined into a single integral layer.

* * * * *